US012570831B2

(12) United States Patent
Ma et al.

(10) Patent No.: US 12,570,831 B2
(45) Date of Patent: Mar. 10, 2026

(54) HYDROGEL-FREE SURFACE FUNCTIONALIZATION FOR SEQUENCING

(71) Applicant: ILLUMINA, INC., San Diego, CA (US)

(72) Inventors: Xiaoyu Ma, San Diego, CA (US); Weixian Xi, San Diego, CA (US); Jeffrey S. Fisher, San Diego, CA (US); Fei Shen, San Diego, CA (US); Wayne N. George, Cambridge (GB); Brian D. Mather, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 941 days.

(21) Appl. No.: 17/838,986

(22) Filed: Jun. 13, 2022

(65) Prior Publication Data

US 2023/0016633 A1    Jan. 19, 2023

Related U.S. Application Data

(60) Provisional application No. 63/210,888, filed on Jun. 15, 2021.

(51) Int. Cl.
*C08K 5/54* (2006.01)
*B01J 19/00* (2006.01)
*C12Q 1/6874* (2018.01)

(52) U.S. Cl.
CPC ............. *C08K 5/54* (2013.01); *B01J 19/0046* (2013.01); *C12Q 1/6874* (2013.01); *B01J 2219/00612* (2013.01); *B01J 2219/00621* (2013.01); *B01J 2219/00626* (2013.01); *B01J 2219/00722* (2013.01)

(58) Field of Classification Search
CPC ................... C08K 5/54; B01J 19/0046; B01J 2219/00612; B01J 2219/00621; B01J 2219/00626; B01J 2219/00722; B01J 2219/00608; B01J 2219/00619; B01J 2219/00725; C12Q 1/6874
See application file for complete search history.

(56) References Cited

U.S. PATENT DOCUMENTS

| 5,130,238 A | 7/1992 | Malek et al. |
| 5,429,807 A | 7/1995 | Matson et al. |

(Continued)

FOREIGN PATENT DOCUMENTS

| EP | 0 742 287 | 11/1996 |
| EP | 0 799 897 | 6/2006 |

(Continued)

OTHER PUBLICATIONS

Bentley et al., Nov. 6, 2008, Accurate whole human genome sequencing using reversible terminator chemistry, Nature, 456:53-59.

(Continued)

*Primary Examiner* — Jennifer Wecker
*Assistant Examiner* — Steven Ray Castaneda
(74) *Attorney, Agent, or Firm* — KNOBBE, MARTENS, OLSON & BEAR, LLP

(57)    ABSTRACT

Embodiments of the present application relate to substrate comprising a surface-bound azido functionalized organosilane wherein the substrate is free or substantially free of a hydrogel or a hydrophilic polymer. Methods of preparing such substrate surface for sequencing applications are also disclosed.

23 Claims, 5 Drawing Sheets

Specification includes a Sequence Listing.

(56) References Cited

U.S. PATENT DOCUMENTS

| 5,436,327 | A | 7/1995 | Southern et al. |
|---|---|---|---|
| 5,455,166 | A | 10/1995 | Walker |
| 5,561,071 | A | 10/1996 | Hollenberg et al. |
| 5,583,211 | A | 12/1996 | Coassin et al. |
| 5,641,658 | A | 6/1997 | Adams |
| 5,658,734 | A | 8/1997 | Brock et al. |
| 5,837,858 | A | 11/1998 | Brennan |
| 5,874,219 | A | 2/1999 | Rava et al. |
| 5,919,523 | A | 7/1999 | Sundberg et al. |
| 6,136,269 | A | 10/2000 | Winkler et al. |
| 6,214,587 | B1 | 4/2001 | Dattagupta et al. |
| 6,287,768 | B1 | 9/2001 | Chenchik et al. |
| 6,287,776 | B1 | 9/2001 | Hefti |
| 6,288,220 | B1 | 9/2001 | Kambara et al. |
| 6,291,193 | B1 | 9/2001 | Khodadoust |
| 6,297,006 | B1 | 10/2001 | Drmanac et al. |
| 6,346,413 | B1 | 2/2002 | Fodor et al. |
| 6,355,431 | B1 | 3/2002 | Chee et al. |
| 6,416,949 | B1 | 7/2002 | Dower et al. |
| 6,482,591 | B2 | 11/2002 | Lockhart et al. |
| 6,514,751 | B2 | 2/2003 | Johann et al. |
| 6,524,793 | B1 | 2/2003 | Chandler et al. |
| 6,610,482 | B1 | 8/2003 | Fodor et al. |
| 6,890,741 | B2 | 5/2005 | Fan et al. |
| 6,913,884 | B2 | 7/2005 | Stuelpnagel et al. |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,582,420 | B2 | 9/2009 | Oliphant et al. |
| 8,951,781 | B2 | 2/2015 | Reed et al. |
| 9,012,022 | B2 | 4/2015 | George et al. |
| 9,815,916 | B2 | 11/2017 | Brown et al. |
| 2002/0055100 | A1 | 5/2002 | Kawashima et al. |
| 2002/0102578 | A1 | 8/2002 | Dickinson et al. |
| 2004/0002090 | A1 | 1/2004 | Mayer et al. |
| 2004/0096853 | A1 | 5/2004 | Mayer |
| 2005/0053980 | A1 | 3/2005 | Gunderson et al. |
| 2005/0064460 | A1 | 3/2005 | Holliger et al. |
| 2005/0130173 | A1 | 6/2005 | Leamon et al. |
| 2005/0181440 | A1 | 8/2005 | Chee et al. |
| 2007/0099208 | A1 | 5/2007 | Drmanac et al. |
| 2007/0128624 | A1 | 6/2007 | Gormley et al. |
| 2008/0009420 | A1 | 1/2008 | Schroth et al. |
| 2008/0108082 | A1 | 5/2008 | Rank et al. |
| 2009/0186349 | A1 | 7/2009 | Gunderson et al. |
| 2010/0111768 | A1 | 5/2010 | Banerjee et al. |
| 2011/0059865 | A1 | 3/2011 | Smith et al. |
| 2013/0116153 | A1 | 5/2013 | Bowen et al. |
| 2013/0165350 | A1 | 6/2013 | Kiumelis et al. |
| 2014/0079923 | A1 | 3/2014 | George et al. |
| 2014/0243224 | A1 | 8/2014 | Barnard et al. |
| 2015/0005447 | A1 | 1/2015 | Berti et al. |
| 2019/0352327 | A1 | 11/2019 | Wu et al. |
| 2019/0360041 | A1 | 11/2019 | Wu et al. |
| 2021/0187470 | A1 | 6/2021 | Yang et al. |

FOREIGN PATENT DOCUMENTS

| WO | WO 91/06678 | 5/1991 |
|---|---|---|
| WO | WO 93/17126 | 9/1993 |
| WO | WO 95/11995 | 5/1995 |
| WO | WO 95/35505 | 12/1995 |
| WO | WO 00/63437 | 10/2000 |
| WO | WO 04/018497 | 3/2004 |
| WO | WO 05/010145 | 2/2005 |
| WO | WO 07/123744 | 11/2007 |
| WO | WO 2014/142841 | 9/2014 |
| WO | WO 2015/085268 | 6/2015 |
| WO | WO 2019/126040 | 6/2019 |

OTHER PUBLICATIONS

Dean et al., Apr. 16, 2002, Comprehensive human genome amplification using multiple displacement amplification, Proc Natl. Acad. Sci. USA, 99(8):5261-5266.

Dressman et al., Jul. 22, 2003, Transforming single DNA molecules into fluorescent magnetic particles for detection and enumeration of genetic variations, Proc. Natl. Acad. Sci. USA 100(15):8817-8822.

Kehagias et al., 2009, Stamp replication for thermal and UV nanoimprint lithography using a UV-sensitive silsesquioxane resist, Microelectronic Engineering, 86:776-778.

Lage et al., 2003, Whole genome analysis of genetic alterations in small DNA samples using hyperbranched strand displacement amplification and array-CGH, Genome Research 13:294-307.

Lizardi et al., Jul. 1998, Mutation detection and single-molecule counting using isothermal rolling-circle amplification, Nat. Genet. 19:225-232.

Walker et al., 1995, A chemiluminescent DNA probe test based on strand displacement amplification, in Molecular Methods for Virus Detection, Wiedbrauk et al., eds., Academic Press, Inc., pp. 329-349.

Walker et al., 1992, Strand displacement amplification—an isothermal, in vitro DNA amplification technique, Nucl. Acids Res. 20(7):1691-1696.

International Search Report and Written Opinion dated Oct. 14, 2022 in International Application No. PCT/US2022/033257.

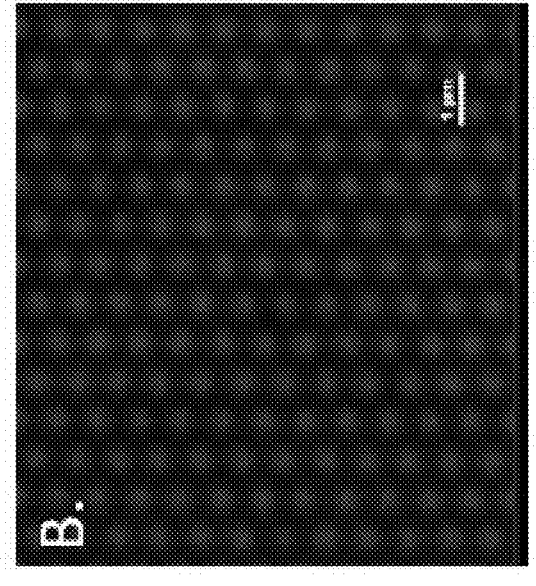
FIG. 6A
FIG. 6B
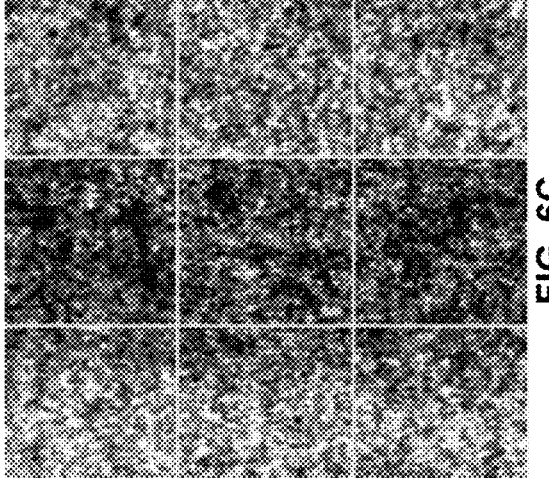
FIG. 6C

SEQUENCE LISTING

<160> NUMBER OF SEQ ID NOS: 10

<210> SEQ ID NO 1
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 1
aatgatacgg cgaccaccga gauctacac                                    29

<210> SEQ ID NO 2
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 2
caagcagaag acggcatacg agat                                         24

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
aatgatacgg cgaccaccga                                              20

<210> SEQ ID NO 4
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 4
caagcagaag acggcatacg a                                            21

<210> SEQ ID NO 5
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 5

-continued

```
aatgatacgg cgaccaccga gatctacac                                    29

<210> SEQ ID NO 6
<211> LENGTH: 27
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: diol linker subject to chemical cleavage
<220> FEATURE:
<223> OTHER INFORMATION: Synthetic Oligonucleotide

<400> SEQUENCE: 6
yyycaagcag aagacggcat acgagat                                      27

<210> SEQ ID NO 7
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 7
gctggcacgt ccgaacgctt cgttaatccg ttgag                             35

<210> SEQ ID NO 8
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 8
cgtcgtctgc catggcgctt cggtggatat gaact                             35

<210> SEQ ID NO 9
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 9
acggccgcta atatcaacgc gtcgaatccg caact                             35

<210> SEQ ID NO 10
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 10
gccgcgttac gttagccgga ctattcgatg cagc                              34
```

HYDROGEL-FREE SURFACE FUNCTIONALIZATION FOR SEQUENCING

FIELD

The present disclosure relates to substrates with functionalized surface for use in detection and/or analysis of biological molecules, such as nucleic acids.

REFERENCE TO SEQUENCE LISTING

The present application is being filed along with a Sequence Listing in electronic format. The Sequence Listing is provided as a file entitled Sequence_listing_ILLINC_564A.txt created Jun. 13, 2022, which is 2.21 KB in size. The information in the electronic format of the Sequence Listing is incorporated herein by reference in its entirety.

BACKGROUND

Polymer-coated substrates are used in many technological applications, including DNA sequencing. In sequencing-by-synthesis (SBS), a surface of a solid support such as flow cell is coated with a polymer such as a functionalized hydrogel for immobilizing primer oligonucleotides such as P5/P7 primers, and enabling DNA clustering. One example of the hydrogel used in SBS is poly(N-(5-azidoacetamidylpentyl) acrylamide-co-acrylamide) (PAZAM). Patterned solid support containing PAZAM may be manufactured using various techniques, including nanoimprinting lithography (NIH). Some of the techniques have been described in U.S. Publication Nos. 2013/0116153, 2014/0079923, 2014/0243224, and 2019/0360041, each of which is incorporated by reference.

In standard patterned surface manufacturing process, a hydrogel gel material or a hydrophilic polymer material can be deposited on the surface and differential hydrophobic/hydrophilic characteristics of the contours and interstitial regions on the surface can be exploited to conveniently remove gel material from some regions of the surface while retaining gel material at desired features. For example, the hydrogel gel material can be retained at silanized wells and removed from hydrophobic interstitial regions around the wells that are coated with hydrophobic fluorinated or perfluorinated polymer(s). Coating a solid support with PAZAM layers not only require multiple steps in the fabrication process, but also may have certain unintended consequences and challenges, such as incomplete lift-off of the extra PAZAM from the interstitial regions.

As such, there exists a need to develop alternative processes for surface functionalization. Historically, DNA clustering and long-cycles of SBS chemistry cannot happen directly on solid support surface, ascribing to the challenges to ensure that the silane layer resembles the polymer that is replacing and that the stability and robustness is comparable.

SUMMARY

Some aspect of the present disclosure relates to a substrate comprising a surface-bound organosilane, wherein the surface-bound organosilane comprises azido groups, each azido group is attached to a silicon atom of the organosilane through a linker moiety, and wherein the substrate is free or substantially free of a hydrogel or a hydrophilic polymer.

Some aspect of the present disclosure relates to a substrate comprising a surface-bound organosilane covalently attached to a plurality of biological molecules, wherein the surface-bound organosilane comprises azido groups that are covalent bonded with the plurality of biological molecules, each azido group is attached to a silicon atom of the organosilane through a linker moiety, and wherein the substrate is free or substantially free of a hydrogel or a hydrophilic polymer.

Additional aspect of the present disclosure relate to a method of functionalizing a surface of a substrate, comprising: depositing an organosilane to the surface of the substrate to form a surface-bound organosilane layer, wherein the surface-bound organosilane layer comprises azido groups, each azido group is attached to a silicon atom of the organosilane through a linker moiety, and wherein the method does not comprise depositing a hydrogel or a hydrophilic polymer to the surface of the substrate prior to or after the deposition of the organosilane.

Additional aspect of the present disclosure relates to a method of immobilizing oligonucleotides to a substrate, comprising:

contacting a plurality of oligonucleotides with an organosilane bound surface of the substrate, wherein the organosilane comprises azido groups, each azido group is attached to a silicon atom of the organosilane through a linker moiety, and wherein the substrate is free or substantially free of a hydrogel or a hydrophilic polymer; and reacting the plurality of the oligonucleotides with the azido groups of the organosilane to covalently attach the oligonucleotides to the substrate.

BRIEF DESCRIPTION OF THE DRAWINGS

FIG. 6A is a fluorescent image of a flowcell surface prepared by a process according to an embodiment of the present disclosure, where the interstitial region of the flowcell surface is polished prior to primer grafting.

FIG. 6B is a fluorescent image of a flowcell surface prepared by a process according to an embodiment of the present disclosure, where the interstitial region of the flowcell surface is polished after primer grafting.

FIG. 6C is a thumbnail image of the flow cell surface after cycle 1 using the process according to FIG. 6A.

DETAILED DESCRIPTION

The present disclosure relates to alternatives processes of preparing the patterned surface for capturing biological molecules of interest, for example, nucleic acid. In particular embodiments, the processes generate polymer-free functionalized surface for sequencing applications. The processes do not involve the use of a hydrogel or a hydrophilic polymer

Figures 1, 2:
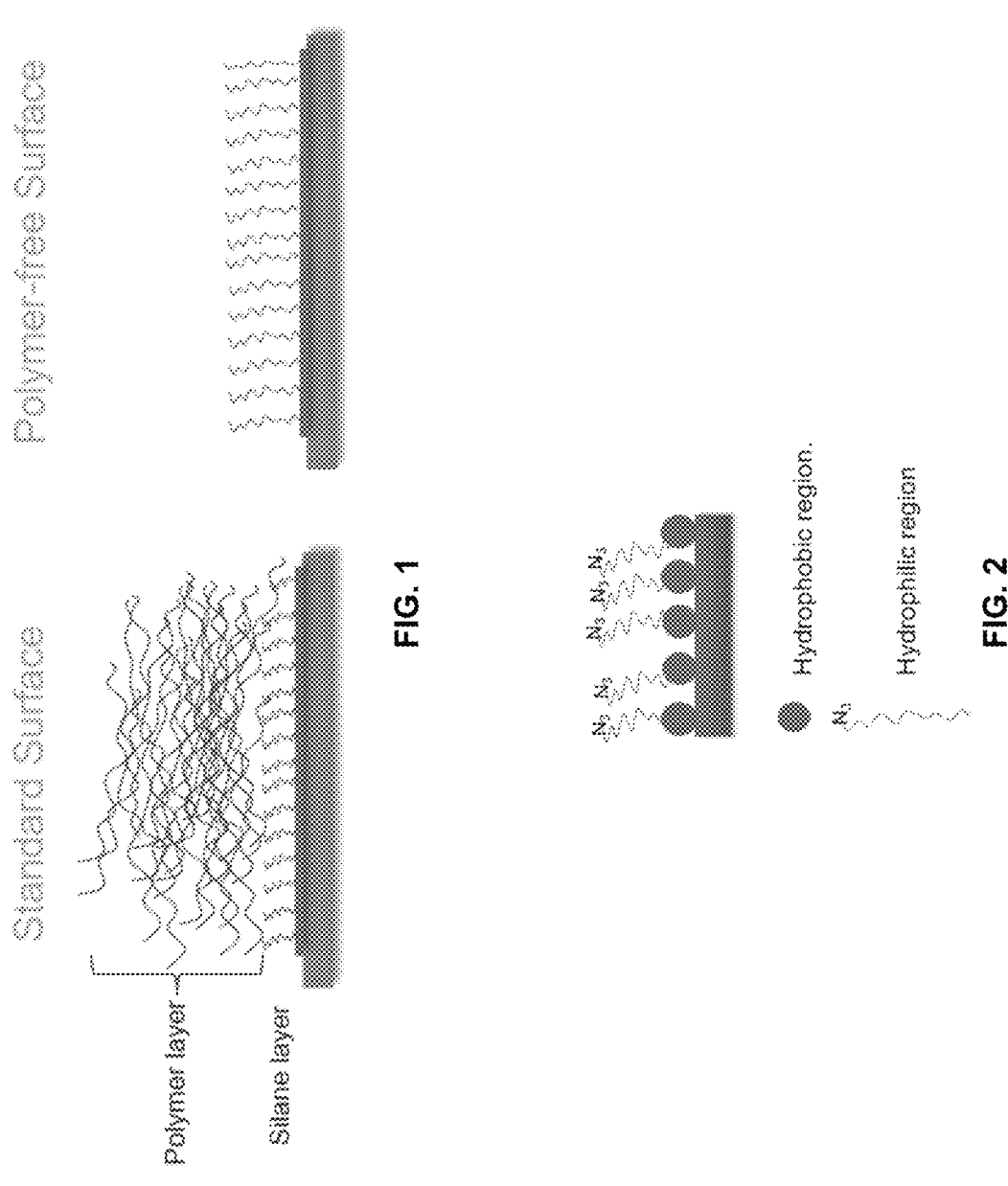
FIG. 1 illustrates a comparison between a substrate surface prepared by a standard process as compared to a polymer-free silanized surface according to an embodiment of the present disclosure.
FIG. 2 is a perspective view of a polymer-free silanized surface of a substrate according to an embodiment of the present disclosure.

3 coating on the surface of the substrate to facilitate the attachment of the biological molecules of interest. In particular embodiments, the process does not use poly(N-(5-azidoacetamidylpentyl)acrylamide-co-acrylamide) (PAZAM). The hydrogel-free surface with no PAZAM layer allows for more simplified substrate fabrication process, as well as avoiding any issues specifically relate to PAZAM. FIG. 1 illustrates a standard PAZAM coated substrate surface in comparison to a PAZAM free surface according to an embodiment of the present disclosure.

The section headings used herein are for organizational purposes only and are not to be construed as limiting the subject matter described.

Definition

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common abbreviations are defined as follows:

CVD Chemical vapor deposition
dATP Deoxyadenosine triphosphate
dCTP Deoxycytidine triphosphate
dGTP Deoxyguanosine triphosphate
dTTP Deoxythymidine triphosphate
PAZAM Poly(N-(5-azidoacetamidylpentyl) acrylamide-co-acrylamide) of any acrylamide to Azapa ratio
SBS Sequencing-by-synthesis As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "array" refers to a population of different probes (e.g., probe molecules) that are attached to one or more substrates such that the different probes can be differentiated from each other according to relative location. An array can include different probes that are each located at a different addressable location on a substrate. Alternatively or additionally, an array can include separate substrates each bearing a different probe, wherein the different probes can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached hydrogel refers to a hydrogel that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, the term "coat," when used as a verb, is intended to mean providing a layer or covering on a surface. At least a portion of the surface can be provided with a layer or cover. In some cases, the entire surface can be provided with a layer or cover. In alternative cases only a portion of the surface will be provided with a layer or covering. The term "coat," when used to describe the relationship between a surface and a material, is intended to mean that the material is present as a layer or cover on the surface. The material can seal the surface, for example, preventing contact of liquid or gas with the surface. However, the material need not form a seal. For example, the material can be porous to liquid, gas, or one or more components carried in a liquid or gas. Exemplary materials that can coat a surface include, but are not limited to, a gel, polymer, organic polymer, liquid, metal, a second surface, plastic, silica, or gas.

As used herein the term "analyte" is intended to include any of a variety of analytes that are to be detected, characterized, modified, synthesized, or the like. Exemplary analytes include, but are not limited to, nucleic acids (e.g., DNA, RNA or analogs thereof), proteins, polysaccharides, cells, nuclei, cellular organelles, antibodies, epitopes, receptors, ligands, enzymes (e g kinases, phosphatases or polymerases), peptides, small molecule drug candidates, or the like. An array can include multiple different species from a library of analytes. For example, the species can be different antibodies from an antibody library, nucleic acids having different sequences from a library of nucleic acids, proteins having different structure and/or function from a library of proteins, drug candidates from a combinatorial library of small molecules, etc.

As used herein the term "contour" is intended to mean a localized variation in the shape of a surface. Exemplary contours include, but are not limited to, wells, pits, channels, posts, pillars, and ridges. Contours can occur as any of a variety of depressions in a surface or projections from a surface. All or part of a contour can serve as a feature in an array. For example, a part of a contour that occurs in a particular plane of a solid support can serve as a feature in that particular plane. In some embodiments, contours are provided in a regular or repeating pattern on a surface.

Where a material is "within" a contour, it is located in the space of the contour. For example, for a well, the material is inside the well, and for a pillar or post, the material covers the contour that extends above the plane of the surface.

In some embodiments, where a second layer is said to "cover" a first layer, the second layer is in the form of a thin film on top of the first layer.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules. The term can be similarly applied to proteins which are distinguishable as different from each other based on amino acid sequence differences.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "feature" means a location in an array that is configured to attach a particular analyte. For example, a feature can be all or part of a contour on a surface. A feature can contain only a single analyte or it can contain a population of several analytes, optionally the several analytes can be the same species. In some embodiments, features are present on a solid support prior to attaching an analyte. In other embodiments the feature is created by attachment of an analyte to the solid support.

As used herein, the term "flow cell" is intended to mean a vessel having a chamber where a reaction can be carried out, an inlet for delivering reagents to the chamber and an outlet for removing reagents from the chamber. In some embodiments, the chamber is configured for detection of the reaction that occurs in the chamber (e.g., on a surface that is in fluid contact with the chamber). For example, the chamber can include one or more transparent surfaces allowing optical detection of arrays, optically labeled molecules, or the like in the chamber. Exemplary flow cells include, but are not limited to those used in a nucleic acid sequencing apparatus such as flow cells for the Genome Analyzer®, MiSeq®, NextSeq® or HiSeq® platforms commercialized by Illumina, Inc. (San Diego, CA); or for the SOLiD® or Ion Torrent® sequencing platform commercialized by Life Technologies (Carlsbad, CA). Exemplary flow cells and methods for their manufacture and use are also described, for example, in WO 2014/142841 A1; U.S. Pat. App. Pub. No. 2010/0111768 A1 and U.S. Pat. No. 8,951,781, each of which is incorporated herein by reference.

As used herein, the term "gel material" is intended to mean a semi-rigid material that is permeable to liquids and gases. Typically, a gel material can swell when liquid is taken up and can contract when liquid is removed, e.g., by drying. Exemplary gels include, but are not limited to, those having a colloidal structure, such as agarose; polymer mesh structure, such as gelatin; or cross-linked polymer structure, such as polyacrylamide, silane free acrylamide (see, for example, US Pat. App. Pub. No. 2011/0059865 A1), PAZAM (see, for example, U.S. Pat. No. 9,012,022, which is incorporated herein by reference), and polymers described in U.S. Patent Pub. No. 2015/0005447, and U.S. application Ser. No. 14/927,252, all of which are incorporated by reference in their entireties. Particularly useful gel material will conform to the shape of a well or other contours where it resides. Some useful gel materials can both (a) conform to the shape of the well or other contours where it resides and (b) have a volume that does not substantially exceed the volume of the well or contours where it resides. In some particular embodiments, the gel material is a polymeric hydrogel.

As used herein, the term "interstitial region" refers to an area in a substrate or on a surface that separates other areas of the substrate or surface. For example, an interstitial region can separate one contour or feature from another contour or feature on the surface. The two regions that are separated from each other can be discrete, lacking contact with each other. In many embodiments the interstitial region is continuous whereas the contours or features are discrete, for example, as is the case for an array of wells in an otherwise continuous surface. The separation provided by an interstitial region can be partial or full separation. Interstitial regions will typically have a surface material that differs from the surface material of the contours or features on the surface. For example, contours of an array can have an amount or concentration of gel material or analytes that exceeds the amount or concentration present at the interstitial regions. In some embodiments the gel material or analytes may not be present at the interstitial regions.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g., found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid, are intended as semantic identifiers for the nucleic acid in the context of a method or composition set forth herein and does not necessarily limit the structure or function of the nucleic acid beyond what is otherwise explicitly indicated. The terms "probe" and "target" can be similarly applied to other analytes such as proteins, small molecules, cells, or the like.

As used herein, the term "fluorinated" refers to a molecule containing at least one fluorine atom. As used herein, the term "perfluorinated" refers to a molecule containing two or more fluorine atoms. In some embodiments, perfluorinated molecules are hydrocarbon-containing molecules in which the hydrogen atoms on sp3-hybridized carbons are replaced with fluorine atoms. For example, certain perfluorinated polymers described herein contain a perfluoroalkyl group or a perfluoroalkylene moiety.

As used herein, the term "photoresist" and derivatives thereof refer to a light-sensitive material used in processes such as photolithography, photoetching, or photoengraving to form a patterned coating on a surface. Photoresist materials change solubility with respect to a developer solution when exposed to certain wavelengths of light. Photoresist layers may be composed of positive (exposed region becomes soluble) or negative (exposed region becomes insoluble) photoresist material.

As used herein, the term "pitch," when used in reference to contours or features on a surface, is intended to refer to the center-to-center spacing for adjacent features. A pattern of features can be characterized in terms of average pitch. The pattern can be ordered such that the coefficient of variation around the average pitch is small or the pattern can be random in which case the coefficient of variation can be relatively large. In either case, the average pitch can be, for example, at least about 10 nm, 0.1 µm, 0.2 µm, 0.3 µm, 0.4 µm, 0.5 µm, 1 µm, 5 µm, 10 µm, 100 µm or more, or a range defined by any of the two preceding values (e.g., 10 to 100 nm, 10 to 200 nm, 200 to 400 nm, 300 to 500 nm). Alternatively or additionally, the average pitch can be, for example, at most about 100 µm, 10 µm, 5 µm, 1 µm, 0.5 µm, 0.1 µm or less, or a range defined by any of the two preceding values. Of course, the average pitch for a particular pattern of features can be between one of the lower values and one of the upper values selected from the ranges above.

As used herein, the term "surface" is intended to mean an external part or external layer of a solid support or gel material. The surface can be in contact with another material such as a gas, liquid, gel, polymer, organic polymer, second surface of a similar or different material, metal, or coat. The surface, or regions thereof, can be substantially flat or planar. The surface can have surface contours such as wells, pits, channels, ridges, raised regions, pegs, posts or the like.

As used herein, the term "depression" refers to a discrete concave feature in a patterned support having a surface opening that is completely surrounded by interstitial region(s) of the patterned support surface. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc.

As used herein, the term "substrate" or "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (e.g., acrylics, polystyrene and copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers. Particularly useful solid supports for some embodiments are components of a flow cell or located within a flow cell apparatus.

As used herein, the term "well" refers to a discrete contour in a solid support having a surface opening that is completely surrounded by interstitial region(s) of the surface. Wells can have any of a variety of shapes at their opening in a surface including but not limited to round, elliptical, square, polygonal, star shaped (with any number of vertices), etc. The cross section of a well taken orthogonally with the surface can be curved, square, polygonal, hyperbolic, conical, angular, etc. In some embodiments, the well is a microwell or a nanowell.

The P5 and P7 primers are used on the surface of commercial flow cells sold by Illumina Inc. for sequencing on the Specific examples of suitable primers include P5 and/or P7 primers, which are used on the surface of commercial flow cells sold by Illumina, Inc., for sequencing on HISEQ™, HISEQX™, MISEQ™, MISEQDX™, MINISEQ™, NEXTSEQ™, NEXTSEQDX™, NOVASEQ™, GENOME ANALYZER™, ISEQ™, and other instrument platforms. The primer sequences are described in U.S. Pat. Pub. No. 2011/0059865 A1, which is incorporated herein by reference. The P5 and P7 primer sequences comprise the following:

```
Paired end set:
P5: paired end 5'→ 3'
                             (SEQ ID NO. 1)
AATGATACGGCGACCACCGAGAUCTACAC P7: paired end 5'→ 3'
                             (SEQ ID NO. 2)
CAAGCAGAAGACGGCATACGAGAT Single read set:
P5: single read: 5'→ 3'
                             (SEQ ID NO. 3)
AATGATACGGCGACCACCGA P7: single read 5'→ 3'
                             (SEQ ID NO. 4)
CAAGCAGAAGACGGCATACGA
```

In some embodiments, the P5 and P7 primers may comprise a linker or spacer at the 5' end. Such linker or spacer may be included in order to permit cleavage, or to confer some other desirable property, for example to enable covalent attachment to a polymer or a solid support, or to act as spacers to position the site of cleavage an optimal distance from the solid support. In certain cases, 10-50 spacer nucleotides may be positioned between the point of attachment of the P5 or P7 primers to a polymer or a solid support. In some embodiments polyT spacers are used, although other nucleotides and combinations thereof can also be used. TET is a dye labeled oligonucleotide having complimentary sequence to the P5/P7 primers. TET can be hybridized to the P5/P7 primers on a surface; the excess TET can be washed away, and the attached dye concentration can be measured by fluorescence detection using a scanning instrument such as a Typhoon Scanner (General Electric). In addition to the P5/P7 primers, other non-limiting examples of the sequencing primer sequences such as P15/P17 primers have also been disclosed in U.S. Publication No. 2019/0352327. In additional, primers PA, PB, PC and PD have been disclosed in U.S. Ser. No. 63/128,663. These additional sequencing primers comprise the following:

P15: 5'→3'
AATGATACGGCGACCACCGAGAT*CTACAC (SEQ. ID. NO. 5), where T* refers to an allyl modified T
P17 primer 5'→3'
YYYCAAGCAGAAGACGGCATACGAGAT (SEQ ID NO. 6), where Y is a diol linker subject to chemical cleavage, for example, by oxidation with a reagent such as periodate, as disclosed in U.S. Publication No. 2012/0309634, which is incorporated by preference in its entirety.

```
PA: 5'→ 3'
                                    (SEQ ID NO. 7)
GCTGGCACGTCCGAACGCTTCGTTAATCCGTTGAG

PB: 5'→ 3'
                                    (SEQ ID NO. 8)
CGTCGTCTGCCATGGCGCTTCGGTGGATATGAACT

PC: 5'→ 3'
                                    (SEQ ID NO. 9)
ACGGCCGCTAATATCAACGCGTCGAATCCGCAACT

PD: 5'→ 3'
                                    (SEQ ID NO. 10)
GCCGCGTTACGTTAGCCGGACTATTCGATGCAGC
```

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH₂—, —CH₂CH₂—, —CH₂CH(CH₃)CH₂—, and the like. Other radical naming conventions clearly indicate that the radical is a di-radical such as "alkylene" or "alkenylene."

As used herein, "$C_a$ to $C_b$" in which "a" and "b" are integers refer to the number of carbon atoms in an alkyl, alkenyl or alkynyl group, or the number of ring atoms of a cycloalkyl or aryl group. That is, the alkyl, the alkenyl, the alkynyl, the ring of the cycloalkyl, and ring of the aryl can contain from "a" to "b", inclusive, carbon atoms. For example, a "$C_1$ to $C_4$ alkyl" group refers to all alkyl groups having from 1 to 4 carbons, that is, CH₃—, CH₃CH₂—, CH₃CH₂CH₂—, (CH₃)₂CH—, CH₃CH₂CH₂CH₂—, CH₃CH₂CH(CH₃)— and (CH₃)₃C—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, alkenyl, alkynyl, cycloalkyl, or aryl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_2$-$C_6$ alkenyl includes $C_2$, $C_3$, $C_4$, $C_5$ and $C_6$ alkenyl, $C_2$-05 alkenyl, $C_3$-$C_4$ alkenyl, etc.; and $C_2$-$C_6$ alkynyl includes $C_2$, $C_3$, $C_4$, $C_5$ and $C_6$ alkynyl, $C_2$-$C_5$ alkynyl, $C_3$-$C_4$ alkynyl, etc.

As used herein, "alkyl" refers to a straight or branched hydrocarbon chain that is fully saturated (i.e., contains no double or triple bonds). The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may be a larger size alkyl having 10 to 30 carbon atoms. The alkyl group may also be a medium size alkyl having 1 to 9 carbon atoms. The alkyl group could also be a lower alkyl having 1 to 6 carbon atoms. By way of example only, "$C_1$-$C_6$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkenyl" refers to a straight or branched hydrocarbon chain containing one or more double bonds. The alkenyl group may have 2 to 30 carbon atoms, although the present definition also covers the occurrence of the term "alkenyl" where no numerical range is designated. The alkenyl group may be a larger size alkenyl having 10 to 30 carbon atoms. The alkenyl group may also be a medium size alkenyl having 2 to 9 carbon atoms. The alkenyl group could also be a lower alkenyl having 2 to 6 carbon atoms. The alkenyl group may be designated as "$C_2$-$C_6$ alkenyl" or similar designations. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, methyl-propen-1-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 30 carbon atoms, although the present definition also covers the occurrence of the term "alkynyl" where no numerical range is designated. The alkynyl group may be a larger size alkynyl having 10 to 30 carbon atoms. The alkynyl group may also be a medium size alkynyl having 2 to 9 carbon atoms. The alkynyl group could also be a lower alkynyl having 2 to 6 carbon atoms. The alkynyl group may be designated as "$C_2$-$C_6$ alkynyl" or similar designations. By way of example only, "$C_2$-$C_6$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 30 carbon atoms, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms.

As used herein, "alkylene" means a branched, or straight chain fully saturated di-radical chemical group containing only carbon and hydrogen that is attached to the rest of the molecule via two points of attachment. The alkylene group may be a larger size alkylene having 10 to 30 carbon atoms. The alkylene group may also be a medium size alkylene having 1 to 9 carbon atoms. The alkylene group could also be a lower alkylene having 1 to 6 carbon atoms.

As used herein, the term "heteroalkylene" refers to an alkylene chain in which one or more skeletal atoms of the alkylene are selected from an atom other than carbon, e.g., oxygen, nitrogen, sulfur, phosphorus or combinations thereof.

As used herein, "alkenylene" means a straight or branched chain di-radical chemical group containing only carbon and hydrogen and containing at least one carbon-carbon double bond that is attached to the rest of the molecule via two points of attachment. The alkenylene group may be a larger size alkenylene having 10 to 30 carbon atoms. The alkenylene group may also be a medium size alkenylene having 2 to 9 carbon atoms. The alkenylene group could also be a lower alkenylene having 2 to 6 carbon atoms.

As used herein, "alkynylene" means a straight or branched chain di-radical chemical group containing only carbon and hydrogen and containing at least one carbon-carbon triple bond that is attached to the rest of the molecule via two points of attachment. The alkynylene group may be a larger size alkynylene having 10 to 30 carbon atoms. The alkynylene group may also be a medium size alkynylene having 2 to 9 carbon atoms. The alkynylene group could also be a lower alkynylene having 2 to 6 carbon atoms.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_6$-$C_{10}$ aryl," "$C_6$ or $C_{10}$ aryl," or similar designations. Examples of aryl groups include, but are not limited to, phenyl, naphthyl, azulenyl, and anthracenyl.

As used herein, "arylene" refers to an aromatic ring or ring system containing only carbon and hydrogen that is attached to the rest of the molecule via two points of attachment.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "heteroarylene" refers to an aromatic ring or ring system containing one or more heteroatoms in the ring backbone that is attached to the rest of the molecule via two points of attachment.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "heterocyclylene" means a non-aromatic cyclic ring or ring system containing at least one heteroatom that is attached to the rest of the molecule via two points of attachment.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_3$-$C_6$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "cycloalkylene" means a fully saturated carbocyclyl ring or ring system that is attached to the rest of the molecule via two points of attachment.

The term "azido" as used herein refers to a —$N_3$ group.

When a group is described as "optionally substituted" it may be either unsubstituted or substituted. Likewise, when a group is described as being "substituted", the substituent may be selected from one or more of the indicated substituents. As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), (aryl)$C_1$-$C_6$ alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), (5-10 membered heteroaryl)$C_1$-$C_6$ alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, —CN, hydroxy, $C_1$-$C_6$ alkoxy, ($C_1$-$C_6$ alkoxy)$C_1$-$C_6$ alkyl, —O($C_1$-$C_6$ alkoxy)$C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy, sulfhydryl (mercapto), halo($C_1$-$C_6$)alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —SO$_3$H, sulfonate, sulfate, sulfino, —OS$_2$C$_{1-4}$alkyl, monophosphate, diphosphate, triphosphate, and oxo (═O). Wherever a group is described as "optionally substituted" that group can be substituted with the above substituents.

The embodiments set forth herein and recited in the claims can be understood in view of the above definitions.

Hydrogel-Free Substrate

Some aspect of the present disclosure relates to a substrate comprising a surface-bound organosilane, wherein the surface-bound organosilane comprises azido groups, each azido group is attached to a silicon atom of the organosilane through a linker moiety, and wherein the substrate is free or substantially free of a hydrogel or a hydrophilic polymer.

In some embodiments, the linker moiety comprises a hydrophobic region and a hydrophilic region. FIG. 2 is a perspective view of a hydrogel-free silanized surface of a substrate according to an embodiment of the present disclosure, where at least a portion of the linker moieties to which the azido groups are attached comprises a hydrophobic region and a hydrophilic region. In some such embodiments, the hydrophilic region of the linker may comprise one or more oxyethylene units. In some such embodiments, the hydrophobic region of the linker may comprise aliphatic carbons (such as $C_1$-$C_{30}$ alkylene, $C_2$-$C_{30}$ alkenylene, or $C_2$-$C_{30}$ alkynylene), either as a straight or a branched chain. In some embodiments, the surface-bound organosilane forms a condense organosilane layer, or at least a partially crosslinked or crosslinked silane layer. In some such embodiments, the silane layer has certain degree of intermolecular crosslinking that may provide protection from unintended hydrolysis. For example, the hydrophobic region may serve as a protection layer against hydrolysis while the hydrophilic region provides desirable condition toward higher amplification efficiency with less non-specific binding. In some embodiments, the degree of crosslinking may be accomplished or controlled by using wet chemistry to introduce the organosilane to surface instead of vapor-phase silane deposition. In other embodiments, the degree of crosslinking may be accomplished or controlled by introducing chemical functionalities in the hydrophilic regions of the organosilane to allow intermolecular interaction. In some embodiments, at least partially crosslinked or crosslinked silane layer provide enhanced surface stability.

In some embodiments, the surface-bound organosilane comprises a plurality of the structure:

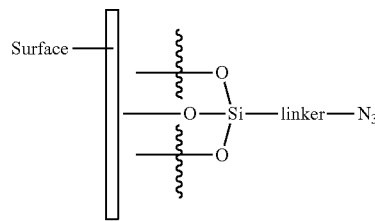

wherein linker comprises optionally substituted alkylene, optionally substituted alkenylene, optionally substituted alkynylene, optionally substituted heteroalkylene, optionally substituted arylene, optionally substituted cycloalkylene, optionally substituted heteroarylene, optionally substituted heterocyclylene, or a combination thereof. In some such embodiments, the linker comprises alkylene or —(CH$_2$CH$_2$O)$_m$—, or a combination thereof, wherein m is an integer of 1 to 10. In one embodiment, the linker moiety comprises a straight chain $C_{11}$ alkylene. As depicted here, the squiggly lines attached to the —O (i.e.,

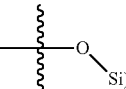

means that this oxygen atom may either attached to the surface, or attached to another silicon atom. In other words, the surface-bound organosilane may have a mono- or a di-oxygen linkage to the surface.

In some embodiments, the surface-bound organosilane is covalently attached to a plurality of biological molecules. In some such embodiments, the plurality of biological molecules comprise nucleosides, nucleotides, oligonucleotides, polynucleotides, peptides, amino acids, or proteins, or combinations thereof. In some embodiments, each of the plurality of biological molecules comprises a functional group that can react with the azido group of the organosilane to form covalent bonding. For example, the biological molecule may comprise an alkynyl group, and the azido group of the surface-bound organosilane forms a triazole moiety with the alkynyl group of the biological molecule:

where the asterisk * indicates the point of attachment of the organosilane to the remaining portion of the biological molecule. In some other embodiments, the biological molecules may be functionalized with other functional groups that can react with the azido groups of the organosilane, for example, halogen, hydroxy, carboxy, epoxy, a cycloalkyne moiety (such as dibenzocyclooctyne group (DBCO) or bicyclo[6.1.0] non-4-yne (BCN)), a cycloalkene (such as norbornene), a heterocycloalkene, or a heterocycloalkyne (such as DBCO-amine), vinyl, acryloyl, nitrene, aldehyde, hydrazinyl, carbene, isocyanate, or maleimide, or combinations thereof.

In some other embodiments, the surface-bound azido containing organosilane is covalently attached to a plurality of biological molecules through a second linker moiety. In some such embodiments, the azido group of the organosilane described herein will first react with a first functional group of a bifunction linker component, then the biological molecule is covalently bonded to the second linker moiety by reacting with a second functional group of the bifunctional linker component. Alternatively, the biological molecule is covalently bonded to the bifunctional linker component by reacting with a first functional group of the bifunctional linker component, then the second functional group of the bifunctional linker plus the biological molecule reacts with the azido group of the organosilane to covalently attach the biological molecule to surface. Similar to the linker moiety of the azido organosilane described herein, the second linker moiety may also contain hydrophilic and/or hydrophobic regions. The hydrophobic region of the second linker moiety may comprise aliphatic carbons (such as $C_1$-$C_{30}$ alkylene, $C_2$-$C_{30}$ alkenylene, or $C_2$-$C_{30}$ alkynylene), either as a straight or a branched chain. The hydrophilic region of the second linker moiety may comprise one or more oxyethylene units (also referred to as the PEG units).

In some embodiments, the linker moiety described herein may also contain a branched structure where one linker moiety is attached to multiple azido groups. In some other embodiments, the linker moiety described herein may converge with one or more linker moieties (each is attached to a different silicon atom, for example the dipodal silane structure), and the azido group is covalently bonded to the position of the convergence of the two or more linker moieties.

In some embodiments, the biological molecules comprise oligonucleotides. In some such embodiments, the plurality of biological molecules are oligonucleotides, each comprising a spacer and an adaptor sequence for hybridization with a template polynucleotide. In some such embodiments, the surface-bound organosilane is covalently attached to a first plurality of first oligonucleotide and a second plurality of a second oligonucleotide. Examples of first and second oligonucleotides as discussed above may comprise primers used in existing SBS processes. Specific examples of suitable primers include P5 and/or P7 primers, which are used on the surface of commercial flow cells sold by Illumina, Inc., for sequencing on HISEQ™, HISEQX™, MISEQ™ MISEQDX™, MINISEQ™, NEXTSEQ™, NEXTSE-QDX™, NOVASEQ™, GENOME ANALYZER™, ISEQ™, and other instrument platforms. The primer sequences are described in U.S. Patent Publication No. 2011/0059865A1, which is incorporated by reference. In some embodiments, a P5 primer include a 5' to 3' oligonucleotide sequence of AATGATACGGCGAC-CACCGAGAUCTACAC (SEQ ID No. 1), AATGA-TACGGCGACCACCGAGATCTACAC (SEQ ID NO. 5), or AATGATACGGCGACCACCGA (SEQ ID No. 3). A P7 primer include a 5' to 3' oligo nucleotide sequence of CAAGCAGAAGACGGCATACGAGAT (SEQ ID No. 2) or CAAGCAGAAGACGGCATACGA (SEQ ID NO. 4). In some further embodiments, the first oligonucleotide comprises the P5 primer sequence. In some further embodiments, the second oligonucleotide comprises the P7 primer sequence. In further embodiments, a portion of the template polynucleotide includes a nucleotide sequence corresponding to or complementary to, a first or second oligonucleotide as disclosed above may have, for example, a sequence corresponding to or complementary to the P5 or P7 primer sequence.

In some embodiments, the spacer of the first or second oligonucleotide comprises 10 to 50 nucleotides, an aliphatic hydrocarbon chain, PEG (i.e., $—(CH_2CH_2O)_n—$, wherein n is an integer of 1 to 10), or a combination thereof. In further embodiments, the space comprises 10 to 50 T nucleotides, $C_{1-10}$ alkylene, or a combination thereof. In specific examples, the space may comprise 10, 15, 20, 25, 30, 35, 40, 45 or 50 T nucleotide and C1, C2, C3, C4, C5, C6 alkylene. In one example, the spacer comprises 30 T nucleotide and $C_3$ alkylene.

A substrate for sequencing application as described herein, may include, as non-limiting examples, substrates used in any of the aforementioned SBS platforms or others. As a non-limiting example, such a substrate may be a flow cell. As used herein, the term "flow cell" is intended to mean a vessel having a chamber (i.e., flow channel) where a reaction can be carried out, an inlet for delivering reagent(s) to the chamber, and an outlet for removing reagent(s) from the chamber. In some examples, the chamber enables the detection of a reaction or signal that occurs in the chamber. For example, the chamber can include one or more transparent surfaces allowing for the optical detection of arrays, optically labeled molecules, or the like, in the chamber. As used herein, a "flow channel" or "flow channel region" may be an area defined between two bonded components, which can selectively receive a liquid sample. In some examples, the flow channel may be defined between a patterned support and a lid, and thus may be in fluid communication with one or more depressions defined in the patterned support. In other examples, the flow channel may be defined between a non-patterned support and a lid. In some embodiments, the substrate is a patterned substrate comprising an array of wells (e.g., nanowells). In such embodiments, the patterned nanowells are separated by interstitial regions, and wherein the plurality of biological molecules reside inside the patterned nanowells.

The term flow cell "support" or "substrate" refers to a support or substrate upon which surface chemistry may be added. The term "patterned substrate" refers to a support in which or on which depressions are defined. The term "non-patterned substrate" refers to a substantially planar support. The substrate may also be referred to herein as a "support," "patterned support," or "non-patterned support." The support may be a wafer, a panel, a rectangular sheet, a die, or any other suitable configuration. The support is generally rigid and is insoluble in an aqueous liquid. The support may be inert to a chemistry that is used to modify the depressions. For example, a support can be inert to chemistry used to form a polymer coating layer, to attach primers such as to a polymer coating layer that has been deposited, etc. Examples of suitable supports include epoxy siloxane, glass and modified or functionalized glass, polyhedral oligomeric silsequioxanes (POSS) and derivatives thereof, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($TaO_5$) or other tantalum oxide(s) ($TaO_x$), hafnium oxide ($HaO_2$), carbon, metals, inorganic glasses, or the like. The support may also be glass or silicon or a silicon-based polymer such as a POSS material, optionally with a coating layer of tantalum oxide or another ceramic oxide at the surface. A POSS material may be that disclosed in Kejagoas et al., Microelectronic Engineering 86 (2009) 776-668, which is incorporated by reference herein in its entirety. In some embodiments, the substrate or solid support comprises glass, modified or functionalized glass, plastics, polysaccharides, nylon, nitrocellulose, resins, silica, silicon, modified silicon, carbon, metals, inorganic glasses, and optical fiber bundles. In particular embodiments, the substrate is a flow cell, a nanoparticle, or a bead, including but not limited to spherical silica beads, inorganic nanoparticles, magnetic nanoparticles, cadmium based dots, and cadmium free dots, or a bead disclosed in Ser. No. 17/130,494.

In an example, depressions may be wells such that the patterned substrate includes an array of wells in a surface thereof. The wells may be micro wells or nanowells. The size of each well may be characterized by its volume, well opening area, depth, and/or diameter.

Each well can have any volume that is capable of confining a liquid. The minimum or maximum volume can be selected, for example, to accommodate the throughput (e.g., multiplexity), resolution, analyte composition, or analyte reactivity expected for downstream uses of the flow cell. For example, the volume can be at least about $1\times10^{-3}$ $\mu m^3$, about $1\times10^{-2}$ $\mu m^3$, about 0.1 $\mu m^3$, about 1 $\mu m^3$, about 10 $\mu m^3$, about 100 $\mu m^3$, or more. Alternatively or additionally, the volume can be at most about $1\times10^4$ $\mu m^3$, about $1\times10^3$ $\mu m^3$, about 100 $\mu m^3$, about 10 $\mu m^3$, about 1 $\mu m^3$, about 0.1 $\mu m^3$, or less. The area occupied by each well opening on a surface can be selected based upon similar criteria as those set forth above for well volume. For example, the area for each well opening on a surface can be at least about $1\times10^{-3}$ $\mu m^2$, about $1\times10^2$ $\mu m^2$, about 0.1 $\mu m^2$, about 1 $\mu m^2$, about 10 $\mu m^2$, about 100 $\mu m^2$, or more. Alternatively or additionally, the area can be at most about $1\times10^3$ $\mu m^2$, about 100 $\mu m^2$, about 10 $\mu m^2$, about 1 $\mu m^2$, about 0.1 $\mu m^2$, about $1\times10^{-2}$ $\mu m^2$, or less. The area occupied by each well opening can be greater than, less than or between the values specified above. The depth of each well can be at least about 0.1 $\mu m$, about 1 $\mu m$, about 10 $\mu m$, about 100 $\mu m$, or more. Alternatively or additionally, the depth can be at most about $1\times10^3$ $\mu m$, about 100 $\mu m$, about 10 $\mu m$, about 1 $\mu m$, about 0.1 $\mu m$, or less. The depth of each well 14' can be greater than, less than or between the values specified above.

In some instances, the diameter of each well can be at least about 50 nm, about 0.1 $\mu m^2$, about 0.5 $\mu m$, about 1 $\mu m$, about 10 $\mu m$, about 100 $\mu m$, or more. Alternatively or additionally, the diameter can be at most about $1\times10^3$ $\mu m$, about 100 $\mu m$, about 10 $\mu m$, about 1 $\mu m$, about 0.5 $\mu m$, about 0.1 $\mu m$, or less (e.g., about 50 nm). The diameter can be about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 900 nm, about 950 nm, about 1 $\mu m$, about 1.25 $\mu m$, about 1.5 $\mu m$, about 1.74 $\mu m$, about 2 $\mu m$, about 2.25 $\mu m$, about 2.5 m, about 2.75 $\mu m$, about 3 $\mu m$, about 3.25 $\mu m$, about 3.5 $\mu m$, about 3.75 $\mu m$, about 4 $\mu m$, about 4.25 $\mu m$, about 4.5 $\mu m$, about 4.75 $\mu m$, about 5 $\mu m$, about 5.25 $\mu m$, about 5.5 $\mu m$, about 5.75 $\mu m$, about 6 $\mu m$, about 6.25 $\mu m$, about 6.5 $\mu m$, about 6.75 $\mu m$, about 7 $\mu m$, about 7.25 $\mu m$, about 7.5 $\mu m$, about 7.75 $\mu m$, about 8 $\mu m$, about 8.25 $\mu m$, about 8.5 $\mu m$, about 8.75 $\mu m$, about 9 $\mu m$, about 9.25 $\mu m$, about 9.5 $\mu m$, or about 9.75 $\mu m$. The diameter of each well can be greater than, less than or between the values specified above. A nanowell as the term is used herein is intended to mean a well with a round opening whose largest diameter is about 1 $\mu m$ or less.

In any embodiments of the substrate described herein, the substrate is free or substantially free of poly(N-(5-azidoacetamidylpentyl)acrylamide-co-acrylamide) (PAZAM).

Some additional aspect of the present disclosure relate to a substrate comprising a surface-bound organosilane covalently attached to a plurality of biological molecules, wherein the surface-bound organosilane comprises azido groups that are covalent bonded with the plurality of biological molecules, each azido group is attached to a silicon atom of the organosilane through a linker moiety, and wherein the substrate is free or substantially free of a hydrogel or a hydrophilic polymer. In some embodiments, the biological molecules are oligonucleotides. In further embodiments, the plurality of biological molecules comprises oligonucleotides, for example, a first plurality of a first oligonucleotide and a second plurality of second oligonucleotides. In further embodiments, the first oligonucleotide comprises the P5 primer sequence described herein. In some further embodiments, the second oligonucleotide comprises the P7 primer sequence described herein. The first and/or the second oligonucleotide may further comprise a spacer as described herein. In further embodiments, the substrate further comprises a plurality of template polynucleotides hybridized at least a portion of the first plurality of the first oligonucleotide and/or at least a portion the second plurality of second oligonucleotides. The template polynucleotides include a nucleotide sequence corresponding to or complementary to, the first or second oligonucleotide as disclosed above may have, for example, a sequence corresponding to or complementary to the P5 or P7 primer sequence. In some further embodiments, the substrate comprises amplified template polynucleotides or complements thereof ("clusters").

A template polynucleotide may be processed as part of a process of obtaining a template polynucleotide from sample. Part of processing may include adding polynucleotide or oligonucleotide sequences, such as to the 5', 3', or both ends of the template to assist in subsequence SBS processing. template polynucleotide may be of any given length suitable for obtaining sequencing information in an SBS process. For example, a template polynucleotide may be about 50 nucleotides in length, about 75 nucleotides in length, about 100 nucleotides in length, about 125 nucleotides in length, about 150 nucleotides in length, about 175 nucleotides in length, about 200 nucleotides in length nucleotides in length, about 225 nucleotides in length, about 250 nucleotides in length, about 275 nucleotides in length, about 300 nucleotides in length, about 325 nucleotides in length, about 350 nucleotides in length, about 375 nucleotides in length, about 400 nucleotides in length, about 425 nucleotides in length, about 450 nucleotides in length, about 475 nucleotides in length, or about 500 nucleotides in length.

Preparation of Hydrogel-Free Surface

Additional aspect of the present disclosure relate to a method of functionalizing a surface of a substrate, comprising: depositing an organosilane to the surface of the substrate to form a surface-bound organosilane layer, wherein the surface-bound organosilane layer comprises azido groups, each azido group is attached to a silicon atom of the organosilane through a linker moiety. In some such embodiments, the method does not comprise depositing a hydrogel or a hydrophilic polymer to the surface of the substrate prior to or after the deposition of the organosilane. In some such embodiments, the organosilane is deposited onto the surface of the substrate by wet chemistry. For example, the organosilane is dissolved in a solvent or solvent mixture and the surface is dipped into the solvent or solvent mixture. In some such embodiments, the organosilane is deposited onto the surface by chemical vapor deposition (CVD). The use of wet chemistry allows for a certain degree of intermolecular crosslinking of the silane layer, which may improve surface stability, template amplification efficiency, and compatibility of the surface with SBS chemistry.

In some embodiments of the method described herein, the surface of the substrate is a patterned surface comprising interstitial regions and nanowells, where the nanowells are separated by interstitial regions, as described herein. In some embodiments, the linker moiety comprises a hydrophobic region and a hydrophilic region as described herein. In some such embodiments, the hydrophilic region of the linker may comprise one or more oxyethylene units. In some such embodiments, the hydrophobic region of the linker may comprise aliphatic carbons (such as $C_1$-$C_{30}$ alkylene, $C_2$-$C_{30}$ alkenylene, or $C_2$-$C_{30}$ alkynylene), either as a straight or a branched chain. In some embodiments, the method described herein provides a condense organosilane layer, or at least a partially crosslinked or crosslinked silane layer. In some embodiments, the surface-bound organosilane comprises a plurality of the structure:

wherein linker comprises optionally substituted alkylene, optionally substituted alkenylene, optionally substituted alkynylene, optionally substituted heteroalkylene, optionally substituted arylene, optionally substituted cycloalkylene, optionally substituted heteroarylene, or optionally substituted heterocyclylene, or a combination thereof. In some such embodiments, the linker moiety comprises alkylene or $-(CH_2CH_2O)_m-$, or a combination thereof, wherein m is an integer of 1 to 10. In one embodiment, the linker moiety comprises a straight chain $C_{11}$ alkylene.

In some embodiments, the method further comprises grafting a plurality of biological molecules on the organosilane layer. In some such embodiments, the plurality of biological molecules comprise nucleosides, nucleotides, oligonucleotides, polynucleotides, peptides, amino acids, or proteins, or combinations thereof. The biological molecules may comprise functional groups that allow for covalent bonding with the azido groups of the organosilane, for example, the functional groups of the biological molecules may include a alkyne moeity, a cycloalkyne moiety (such as dibenzocyclooctyne group (DBCO) or bicyclo[6.1.0] non-4-yne (BCN)), a cycloalkene (such as norbornene), a heterocycloalkene, or a heterocycloalkyne (such as DBCO-amine), vinyl, acryloyl, nitrene, aldehyde, hydrazinyl, carbene, isocyanate, or maleimide, or combinations thereof. In one embodiment, each of the plurality of oligonucleotides comprises an alkynyl group, and the azido group of the organosilane forms a triazole moiety with the alkynyl group of the oligonucleotide. In further embodiments, the biological molecules are a plurality of oligonucleotides. In some such embodiments, the oligonucleotides each comprises a spacer and an adaptor sequence for hybridization with a template polynucleotide. In some further embodiments, the plurality of oligonucleotides comprise a first plurality of a first oligonucleotide and a second plurality of second oligonucleotides as described herein. In further embodiments, the first oligonucleotide comprises the P5 primer sequence described herein. In some further embodiments, the second oligonucleotide comprises the P7 primer sequence described herein. The first and/or the second oligonucleotide may further comprise a spacer as described herein. In some embodiments, the spacer of the first or second oligonucleotide comprises 10 to 50 nucleotides, an aliphatic hydrocarbon chain, PEG (i.e., $-(CH_2CH_2O)_n-$, wherein n is an integer of 1 to 10), or combinations thereof. In further embodiments, the space comprises 10 to 50 T nucleotides, $C_{1-10}$ alkylene, or a combination thereof. In specific examples, the space may comprise 10, 15, 20, 25, 30, 35, 40, 45 or 50 T nucleotide and C1, C2, C3, C4, C5, C6 alkylene. In one example, the spacer comprises 30 T nucleotide and $C_3$ alkylene.

In some embodiments, the method may comprise attaching a bifunctional linker component described herein to the azido group prior to grafting the biological molecule. As such, the surface-bound azido containing organosilane is covalently attached to each of the biological molecules through a second linker moiety. Alternatively, the bifunctional linker component is first covalently attached to each of the biological molecules by reacting a first functional group of the bifunctional linker component with a functional group of the biological molecule, then the biological molecules is grafted on the surface by reacting the remaining functional group of the bifunctional linker component with the azido group of the surface-bound organosilane.

In some embodiments, the method further comprises removing the organosilane layer from the interstitial regions such that the organosilane is only present inside the nanowells prior to grafting the oligonucleotides. In some other embodiments, the organosilane and oligonucleotides are removed from the interstitial regions after grafting the plurality of the oligonucleotides. The removal of the organosilane from the surface either before or after grafting of the biological molecules may be achieved by a polishing step.

Figure 3:
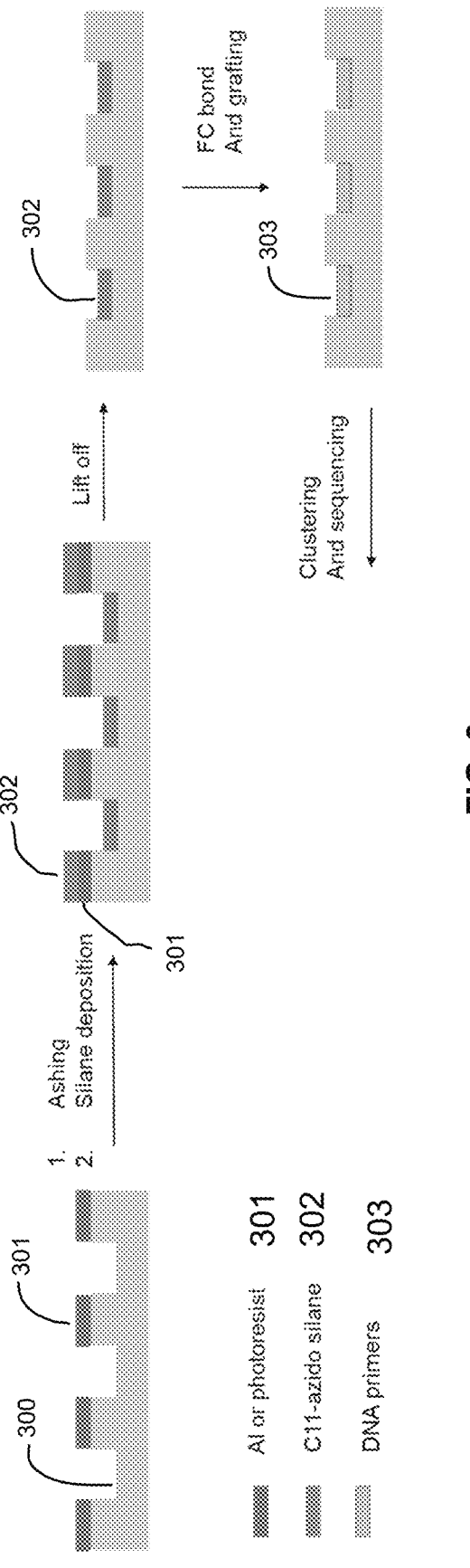
FIG. 3 illustrates a polish-free workflow of preparing a substrate surface for a sequencing application according to an embodiment of the present disclosure.

As an alternative to the method that involving a polishing step to remove the organosilane layer from the interstitial regions of the patterned surface, FIG. 3 illustrates a lift-off patterning workflow for creating a patterned surface. First, a sacrificial layer such as aluminum (Al) or a photoresist 301 is selectively deposited on the interstitial regions of the surface. Then, an organosilane (e.g., the azido silane 302) as described herein is deposited on the whole surface of the substrate, including both the nanowells 300 and the interstitial regions. Third, the sacrificial layer on the interstitial regions (including the organosilane deposited on top of the sacrificial layer) is lift off, leaving the remaining azido silane 302 in the nanowells 300 for reaction with the oligonucleotides 303 (e.g., P5/P7 primers), and downstream applications such as clustering the sequencing. The type of substrate may be used in this polish-free workflow is not limited to NIL or glass substrates. Surfaces containing other materials such as polyhedral oligomeric silsequioxanes (POSS) and derivatives thereof, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($TaO_5$) or other tantalum oxide(s) ($TaO_x$), hafnium oxide ($HaO_2$), carbon, metals, inorganic glasses, or the like may also be used.

Additional aspect of the present disclosure relates to a method of immobilizing oligonucleotides to a substrate, comprising:

contacting a plurality of oligonucleotides with an organosilane bound surface of the substrate as described herein (e.g., a patterned substrate comprising a plurality of nanowells separated by interstitial regions), wherein the organosilane comprises azido groups, each azido group is attached to a silicon atom of the organosilane through a linker moiety, and wherein the substrate is free or substantially free of a hydrogel or a hydrophilic polymer; and reacting the plurality of the oligonucleotides with the azido groups of the organosilane to covalently attach the oligonucleotides to the substrate.

In some embodiments, each of the plurality of oligonucleotides comprises a spacer and an adaptor sequence complementary to at least a portion of a template polynucleotide sequence. In some such embodiments, the plurality of oligonucleotides comprises a first plurality of a first oligonucleotide and a second plurality of second oligonucleotides as described herein. In further embodiments, the first oligonucleotide comprises a spacer and the P5 primer sequence described herein. In some further embodiments, the second oligonucleotide comprises a space and the P7 primer sequence described herein. In some embodiments, the spacer of the first or second plurality of oligonucleotides comprises 10 to 50 nucleotides, an aliphatic hydrocarbon chain, or a combination thereof. In further embodiments, the space comprises 10 to 50 T nucleotides, $C_{1-10}$ alkylene, or a combination thereof. In specific examples, the space may comprise 10, 15, 20, 25, 30, 35, 40, 45 or 50 T nucleotide and C1, C2, C3, C4, C5, C6 alkylene. In one example, the spacer comprises 30 T nucleotide and $C_3$ alkylene. In any embodiments of the spacer of the oligonucleotide (e.g., primers) described herein, the spacer comprises at least 7 nucleotides in length. In further embodiments, the spacer is at least 10, 15, 20, 25, or 30 nucleotides in length. In some embodiments, the concentration of the first and/or second oligonucleotide is about 1 µM to about 100 µM, about 2 µM to about 50 µM, about 5 µM to about 25 µM, or about 10 µM (grafting concentration).

In some embodiments, the method further comprises contacting the immobilized oligonucleotides with a plurality of template polynucleotides; and amplifying the template polynucleotides. In some embodiments, the amplification method comprises Illumina's ExAmp (exclusion amplification). Exclusion amplification allows simultaneous seeding (landing of the DNA strand in the nanowell) and amplification during cluster generation, which reduces the chances of multiple library fragments amplifying in a single cluster. The amplification process is also known as clustering process. For a clustering procedure, a modification may be made to a template polynucleotide such as during sample preparation to include one or more nucleotide sequences at one or both of its 3' and 5' ends. For example, each template comprising at the 3' end a sequence capable of hybridizing to the first oligonucleotide and at the 5' end a sequence the complement of which is capable of hybridizing to the second oligonucleotide. A copy or copies of the template nucleotide and nucleotide sequences complementary to the template nucleotide may then be synthesized on the surface of the substrate, forming a cluster. In some such embodiments, such clustering may result in formation of a monoclonal cluster. The amplification the plurality of different template polynucleotides using the first oligonucleotides and the second oligonucleotides generates a clustered array of polynucleotides.

In some embodiments, the amplification method comprises flowing a solution of the free first oligonucleotide onto the oligonucleotide grafted surface during ExAmp. In some further embodiments, the concentration of the first oligonucleotide in the solution is about 1 µM to about 100 µM, about 2 µM to about 50 µM, about 5 µM to about 25 µM, or about 10 µM (grafting concentration).

In some embodiments, the substrate comprises a flow cell. In other embodiments, the substrate is a nanoparticle or a bead, and SBS then occurs on the particles.

In any embodiments of the methods described herein, the method does not include depositing a hydrogel or hydrophilic polymer to the surface to facilitate the capture of biological molecules of interest (e.g., oligonucleotide primers).

Sequencing Applications

Some embodiments are directed to methods of detecting an analyte using a substrate with a patterned surface prepared by the methods described herein. In some embodiments, the analyte is selected from nucleic acids, polynucleotides, proteins, antibodies, epitopes to antibodies, enzymes, cells, nuclei, cellular organelles, or small molecule drugs. In one embodiment, the analyte is a polynucleotide. In one embodiment, the detecting includes determining a nucleotide sequence of the polynucleotide.

Some embodiments that use nucleic acids can include a step of amplifying the nucleic acids on the substrate. Many different DNA amplification techniques can be used in conjunction with the substrates described herein. Exemplary techniques that can be used include, but are not limited to, polymerase chain reaction (PCR), rolling circle amplification (RCA), multiple displacement amplification (MDA), or random prime amplification (RPA). In particular embodiments, one or more oligonucleotide primers used for amplification can be attached to a substrate (e.g. via the azido silane layer). In PCR embodiments, one or both of the primers used for amplification can be attached to the substrate. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference.

PCR amplification can also be carried out with one amplification primer attached to a substrate and a second primer in solution. An exemplary format that uses a combination of one attached primer and soluble primer is emulsion PCR as described, for example, in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference. Emulsion PCR is illustrative of the format, and it will be understood that for purposes of the methods set forth herein the use of an emulsion is optional and indeed for several embodiments an emulsion is not used. Furthermore, primers need not be attached directly to substrate or solid supports as set forth in the ePCR references and can instead be attached to a gel or polymer coating as set forth herein.

RCA techniques can be modified for use in a method of the present disclosure. Exemplary components that can be used in an RCA reaction and principles by which RCA produces amplicons are described, for example, in Lizardi et al., *Nat. Genet.* 19:225-232 (1998) and US 2007/0099208 A1, each of which is incorporated herein by reference. Primers used for RCA can be in solution or attached to a gel or polymer coating.

MDA techniques can be modified for use in a method of the present disclosure. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., Nucl. Acids Res. 20:1691-96 (1992); U.S. Pat. Nos. 5,455,166; 5,130,238; and 6,214,587, each of which is incorporated herein by reference. Primers used for MDA can be in solution or attached to a gel or polymer coating.

In particular embodiments a combination of the above-exemplified amplification techniques can be used. For example, RCA and MDA can be used in a combination wherein RCA is used to generate a concatameric amplicon in solution (e.g., using solution-phase primers). The amplicon can then be used as a template for MDA using primers that are attached to a substrate (e.g., via a gel or polymer coating). In this example, amplicons produced after the combined RCA and MDA steps will be attached to the substrate.

Substrates of the present disclosure that contain nucleic acid arrays can be used for any of a variety of purposes. A particularly desirable use for the nucleic acids is to serve as capture probes that hybridize to target nucleic acids having complementary sequences. The target nucleic acids once hybridized to the capture probes can be detected, for example, via a label recruited to the capture probe. Methods for detection of target nucleic acids via hybridization to capture probes are known in the art and include, for example, those described in U.S. Pat. No. 7,582,420; 6,890, 741; 6,913,884 or 6,355,431 or U.S. Pat. Pub. Nos. 2005/0053980 A1; 2009/0186349 A1 or 2005/0181440 A1, each of which is incorporated herein by reference. For example, a label can be recruited to a capture probe by virtue of hybridization of the capture probe to a target probe that bears the label. In another example, a label can be recruited to a capture probe by hybridizing a target probe to the capture probe such that the capture probe can be extended by ligation to a labeled oligonucleotide (e.g., via ligase activity) or by addition of a labeled nucleotide (e.g., via polymerase activity).

In some embodiments, a substrate described herein can be used for determining a nucleotide sequence of a polynucleotide. In such embodiments, the method can comprise the steps of (a) contacting a substrate-attached polynucleotide/copy polynucleotide complex with one or more different type of nucleotides in the presence of a polymerase (e.g., DNA polymerase); (b) incorporating one type of nucleotide to the copy polynucleotide strand to form an extended copy polynucleotide; (c) perform one or more fluorescent measurements of one or more the extended copy polynucleotides; wherein steps (a) to (c) are repeated, thereby determining the sequence of the substrate-attached polynucleotide.

Nucleic acid sequencing can be used to determine a nucleotide sequence of a polynucleotide by various processes known in the art. In a preferred method, sequencing-by-synthesis (SBS) is utilized to determine a nucleotide sequence of a polynucleotide attached to a surface of a substrate (e.g., via any one of the polymer coatings described herein). In such a process, one or more nucleotides are provided to a template polynucleotide that is associated with a polynucleotide polymerase. The polynucleotide polymerase incorporates the one or more nucleotides into a newly synthesized nucleic acid strand that is complementary to the polynucleotide template. The synthesis is initiated from an oligonucleotide primer that is complementary to a portion of the template polynucleotide or to a portion of a universal or non-variable nucleic acid that is covalently bound at one end of the template polynucleotide. As nucleotides are incorporated against the template polynucleotide, a detectable signal is generated that allows for the determination of which nucleotide has been incorporated during each step of the sequencing process. In this way, the sequence of a nucleic acid complementary to at least a portion of the template polynucleotide can be generated, thereby permitting determination of the nucleotide sequence of at least a portion of the template polynucleotide.

Flow cells provide a convenient format for housing an array that is produced by the methods of the present disclosure and that is subjected to a sequencing-by-synthesis (SBS) or other detection technique that involves repeated delivery of reagents in cycles. For example, to initiate a first SBS cycle, one or more labeled nucleotides, DNA polymerase, etc., can be flowed into/through a flow cell that houses a nucleic acid array made by methods set forth herein. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., Nature 456: 53-59 (2008), WO 04/018497; U.S. Pat. No. 7,057,026; WO 91/06678; WO 07/123744; U.S. Pat. Nos. 7,329,492; 7,211, 414; 7,315,019; 7,405,281, and US 2008/0108082, each of which is incorporated herein by reference in its entirety.

In some embodiments of the above-described method, which employ a flow cell, only a single type of nucleotide is present in the flow cell during a single flow step. In such embodiments, the nucleotide can be selected from the group consisting of dATP, dCTP, dGTP, dTTP, and analogs thereof. In other embodiments of the above-described method which employ a flow cell, a plurality different types of nucleotides are present in the flow cell during a single flow step. In such methods, the nucleotides can be selected from dATP, dCTP, dGTP, dTTP, and analogs thereof.

Determination of the nucleotide or nucleotides incorporated during each flow step for one or more of the polynucleotides attached to the polymer coating on the surface of the substrate present in the flow cell is achieved by detecting a signal produced at or near the polynucleotide template. In some embodiments of the above-described methods, the detectable signal comprises an optical signal. In other embodiments, the detectable signal comprises a non-optical signal. In such embodiments, the non-optical signal comprises a change in pH at or near one or more of the polynucleotide templates.

Applications and uses of substrates of the present disclosure have been exemplified herein with regard to nucleic acids. However, it will be understood that other analytes can be attached to a substrate set forth herein and analyzed. One or more analytes can be present in or on a substrate of the present disclosure. The substrates of the present disclosure are particularly useful for detection of analytes, or for carrying out synthetic reactions with analytes. Thus, any of a variety of analytes that are to be detected, characterized, modified, synthesized, or the like can be present in or on a substrate set forth herein. Exemplary analytes include, but are not limited to, nucleic acids (e.g., DNA, RNA or analogs thereof), proteins, polysaccharides, cells, antibodies, epitopes, receptors, ligands, enzymes (e.g., kinases, phosphatases or polymerases), small molecule drug candidates, or the like. A substrate can include multiple different species from a library of analytes. For example, the species can be different antibodies from an antibody library, nucleic acids having different sequences from a library of nucleic acids, proteins having different structure and/or function from a library of proteins, drug candidates from a combinatorial library of small molecules, etc.

In some embodiments, analytes can be distributed to features on a substrate such that they are individually resolvable. For example, a single molecule of each analyte can be present at each feature. Alternatively, analytes can be present as colonies or populations such that individual molecules are not necessarily resolved. The colonies or populations can be homogenous with respect to containing only a single species of analyte (albeit in multiple copies). Taking nucleic acids as an example, each feature on a substrate can include a colony or population of nucleic acids and every nucleic acid in the colony or population can have the same nucleotide sequence (either single stranded or double stranded). Such colonies can be created by cluster amplification or bridge amplification as set forth previously herein. Multiple repeats of a target sequence can be present in a single nucleic acid molecule, such as a concatamer created using a rolling circle amplification procedure. Thus, a feature on a substrate can contain multiple copies of a single species of an analyte. Alternatively, a colony or population of analytes that are at a feature can include two or more different species. For example, one or more wells on a substrate can each contain a mixed colony having two or more different nucleic acid species (i.e., nucleic acid molecules with different sequences). The two or more nucleic acid species in a mixed colony can be present in non-negligible amounts, for example, allowing more than one nucleic acid to be detected in the mixed colony.

EXAMPLES

Additional embodiments are disclosed in further detail in the following examples, which are not in any way intended to limit the scope of the claims.

Example 1

Preparation of Hydrogel-Free Organosilane Surface

Figure 4:
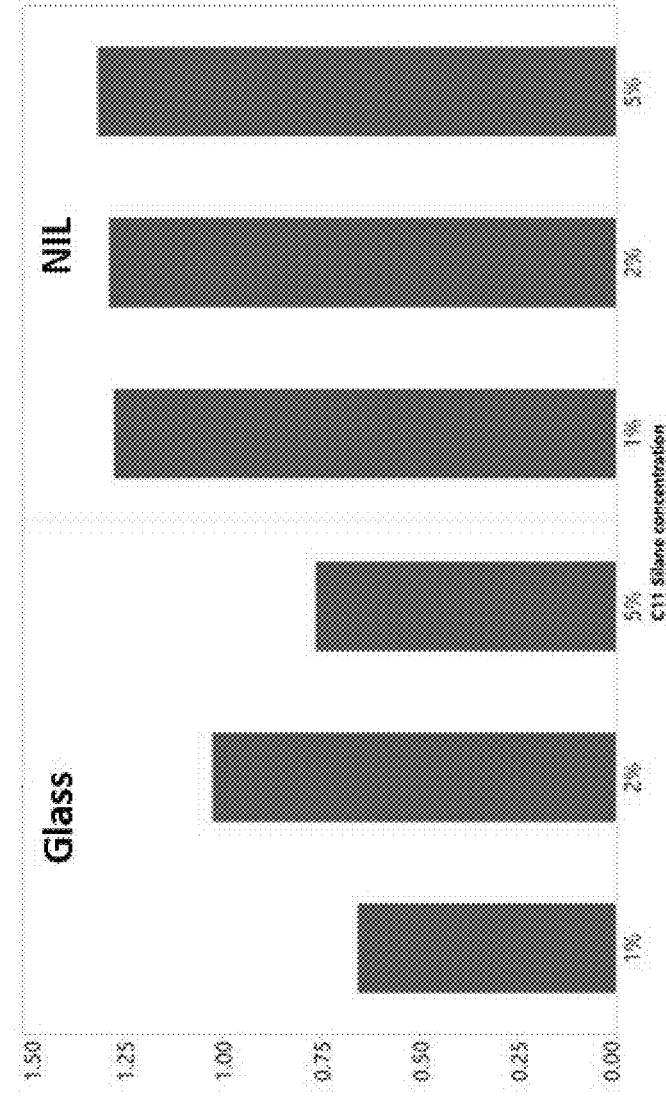
FIG. 4 illustrates the stability testing results on polymer-free azido silane functionalized glass or nanoimprinting lithography (NIL) polymer resin surface of a substrate.

In this example, NIL and glass substrate were treated with 11-azidoundecyltrimethoxysilane (C11-azido). In particular, the substrate was dipped into about 1%-20% C11-azido silane in ethanol for varied time, depending on the concentration of the C11-azido silane solution. When C11-azido silane solution has a higher concentration such as 20%, the substrate was only dipped into the silane solution for about 5 minutes. When C11-azido silane solution has a lower concentration such as 1%-5%, then the substrate was dipped into the silane solution overnight. Alkyne functionalized P5 and P7 primers each containing a 30 Ts plus 3 carbons spacer (T30-SPC$_3$) spacer were grafted via click chemistry with the grafting concentration at 10 μM. Stability was evaluated through hybridization of dye-labeled complementary oligos (CFR) post and pre-stress test. The so-called stress test involves repetitively flowing in HT1 and HT2 buffer along with several temperature cycles up to 96° C. and cool down to 40° C. As shown in FIG. 4, y axis is the ratio of fluorescence intensity of dye-labeled QC oligos post and pre-stress test. It was observed that the azido silanized NIL surface has better stability as compared to pure glass surface, as the value of fluorescence ratio is above 1 upon the treatment of silane at different concentrations on NIL substrate.

Example 2

Primer Grafting on Hydrogel-Free Surface

Figure 5:
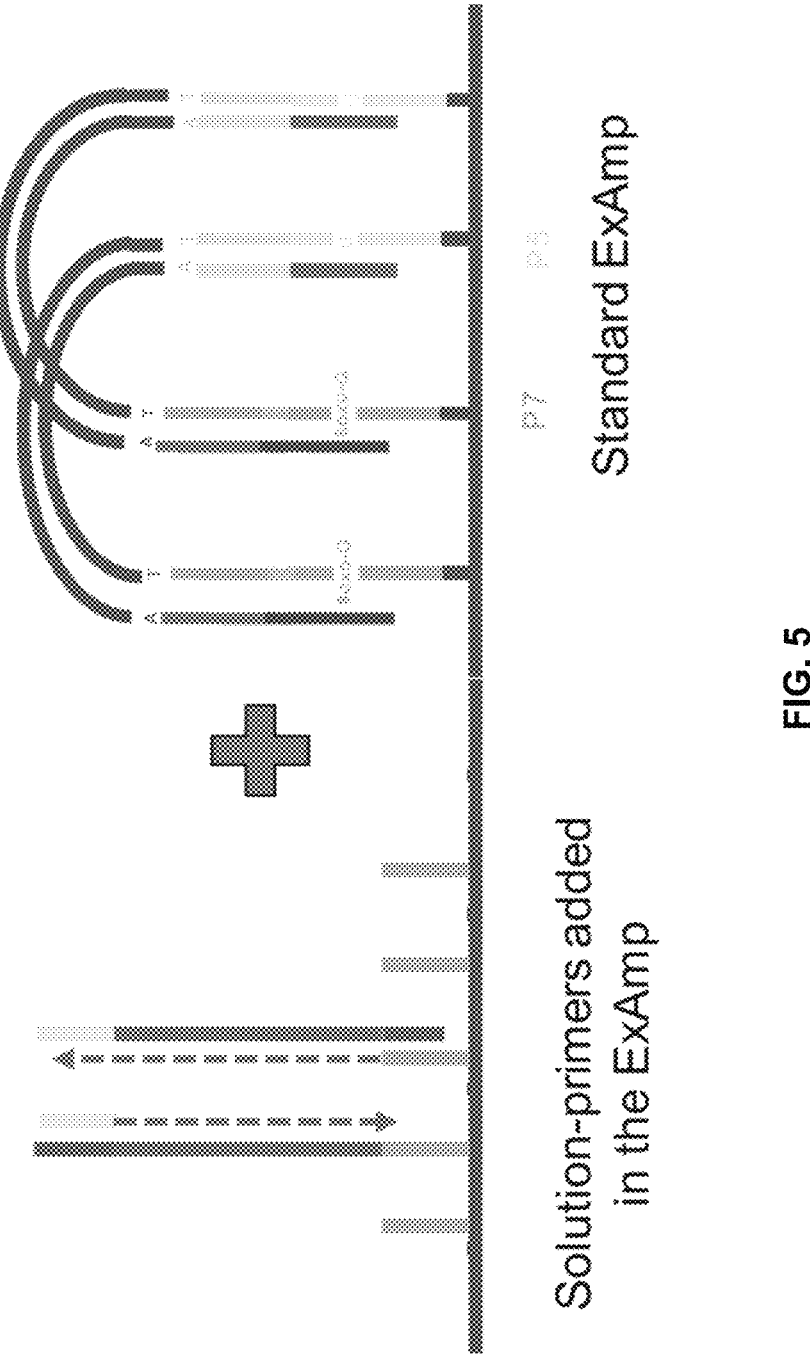
FIG. 5 illustrates the hybrid clustering schedule when solution P5 primer in used in combination with the standard exclusion amplification (ExAmp) surface clustering.

Illumina's standard ExAmp clustering method utilizes a lawn of P5 and P7 primers with 6 Ts as spacer for DNA amplification on PAZAM coated substrate. However, this method led to extremely low clustering/sequencing intensity as directly on non-PAZAM substrate described herein. Herein, a novel hybrid clustering methodology has been developed and illustrated in FIG. 5. The first and the second oligonucleotide primers that were grafted onto the azido-silanized surface (i.e., P5 and P7) each contains a T30-SPC$_3$ spacer. In particular, the lawn of the flow cell was first immobilized with T30-SPC$_3$-P5 and T30-SPC$_3$-P7 primers. In addition, 10 μM free P5 primers (with no spacer) was added to the ExAmp buffer solution containing the poly-merase for ExAmp-based amplification to enhance the amplification efficiency. "ExAmp" surface clustering is a recombinase polymerase DNA amplification method, which applies enzyme formulation for the amplification. The T30-SPC$_3$ spacer provides flexibility hybridization/extension of the lawn P5 and P7 primers and also offered certain degree of rigidity.

To obtain the sequencing signals only from the nanowells, a polishing step was performed prior to DNA clustering.

Two different processing approaches have been tested: (1) polishing the organosilane layer at the interstitial area before grafting; (2) polishing primers/organosilane layer at the interstitial area after grafting. FIG. 6A and FIG. 6B are the fluorescence images under confocal microscope showing the DNA clusters only exist in the nano well, where the fluorescence signal comes from the hybridization of dye labeled SBS3 primer, following processing approaches (1) and (2) respectively. FIG. 6C is the thumbnail image of the flow cell surface after cycle 1 of sequencing, illustrating the presence of the DNA clusters on the substrate surface, where the surface is prepared by polishing the organosilane layer at the interstitial area before primer grafting.

---

What is claimed is:

1. A substrate comprising a surface-bound organosilane covalently attached to a plurality of biological molecules, wherein the surface-bound organosilane comprises azido groups that are covalent bonded with the plurality of biological molecules, each azido group is attached to a silicon atom of the organosilane through a linker moiety, and wherein the substrate is free or substantially free of a hydrogel or a hydrophilic polymer.

2. The substrate of claim 1, wherein the linker moiety comprises a hydrophobic region and a hydrophilic region.

3. The substrate of claim 1, the surface-bound organosilane comprises a plurality of the structure:

wherein linker comprises optionally substituted alkylene, optionally substituted alkenylene, optionally substituted alkynylene, optionally substituted heteroalkylene, optionally substituted arylene, optionally substituted cycloalkylene, optionally substituted heteroarylene, or optionally substituted heterocyclylene, or combinations thereof.

4. The substrate of claim 1, wherein the linker moiety comprises alkylene or —$(CH_2CH_2O)_m$—, or a combination thereof, wherein m is an integer of 1 to 10.

5. The substrate of claim 1, each of the plurality of biological molecules comprises an alkynyl group, a DBCO moiety or a BCN moiety, and the azido group of the surface-bound organosilane forms a triazole moiety with the biological molecule.

6. The substrate of claim 5, wherein the plurality of biological molecules comprise nucleosides, nucleotides, oligonucleotides, polynucleotides, peptides, amino acids, or proteins, or combinations thereof.

7. The substrate of claim 6, wherein the plurality of biological molecules are oligonucleotides, each comprising a spacer and an adaptor sequence for hybridization with a template polynucleotide.

8. The substrate of claim 7, wherein the spacer comprises 10 to 50 T nucleotides, $C_{1-10}$ alkylene, PEG, or a combination thereof.

9. The substrate of claim 8, wherein the spacer comprises 30 T nucleotide and $C_3$ alkylene.

10. The substrate of claim 1, wherein the substrate is a flow cell, a nanoparticle, or a bead.

11. The substrate of claim 1, wherein the substrate comprises patterned nanowells separated by interstitial regions, and wherein the plurality of biological molecules reside inside the patterned nanowells.

12. A method of functionalizing a surface of a substrate, comprising:
   depositing an organosilane to the surface of the substrate to form a surface-bound organosilane layer, wherein the surface-bound organosilane layer comprises azido groups, each azido group is attached to a silicon atom of the organosilane through a linker moiety, and wherein the method does not comprise depositing a hydrogel or a hydrophilic polymer to the surface of the substrate prior to or after the deposition of the organosilane.

13. A method of immobilizing oligonucleotides to a substrate, comprising:
   contacting a plurality of oligonucleotides with an organosilane bound surface of the substrate, wherein the organosilane comprises azido groups, each azido group is attached to a silicon atom of the organosilane through a linker moiety, and wherein the substrate is free or substantially free of a hydrogel or a hydrophilic polymer; and
   reacting the plurality of the oligonucleotides with the azido groups of the organosilane to covalently attach the oligonucleotides to the substrate.

14. The method of claim 13, wherein the substrate comprising a plurality of nanowells separated by interstitial regions.

15. The method of claim 14, further comprising removing the oligonucleotides from the interstitial regions of the surface such that the oligonucleotides are only present inside the nanowells.

16. The method of claim 13, wherein each of the plurality of oligonucleotides comprises an alkynyl group, a DBCO moiety, or a BCN moiety, and the azido group of the organosilane forms a triazole moiety with the oligonucleotide.

17. The method of claim 13, wherein each of the plurality of oligonucleotides comprises a spacer and an adaptor sequence complementary to at least a portion of a template polynucleotide sequence.

18. The method of claim 17, wherein the spacer comprises 10 to 50 T nucleotides, $C_{1-10}$ alkylene, or a combination thereof.

19. The method of claim 18, wherein the spacer comprises 30 T nucleotide and $C_3$ alkylene.

20. The method of claim 13, further comprising contacting the immobilized oligonucleotides with a plurality of template polynucleotides; and amplifying the template polynucleotides.

21. The method of claim 13, wherein the linker moiety comprises a hydrophobic region and a hydrophilic region.

22. The method of claim 13, the linker moiety comprises optionally substituted alkylene, optionally substituted alkenylene, optionally substituted alkynylene, optionally substituted heteroalkylene, optionally substituted arylene, optionally substituted cycloalkylene, optionally substituted heteroarylene, or optionally substituted heterocyclylene, or combinations thereof.

23. The method of claim 22, wherein the linker moiety comprises alkylene or —$(CH_2CH_2O)_m$—, or a combination thereof, wherein m is an integer of 1 to 10.

* * * * *